United States Patent [19]
Barreau et al.
[11] Patent Number: 4,994,470
[45] Date of Patent: Feb. 19, 1991

[54] BENZOPYRAN DERIVATIVES AND PHARMACEUTICAL COMPOSITIONS CONTAINING THEM

[75] Inventors: Michel Barreau, Montgeron; Jean-Claude Hardy, Cergy Pontoise; Christian Renault, Taverny, all of France

[73] Assignee: Rhone-Poulenc Sante, Antony, France

[21] Appl. No.: 465,448

[22] Filed: Jan. 16, 1990

[30] Foreign Application Priority Data

Jan. 20, 1989 [FR] France ................................ 89 00656

[51] Int. Cl.[5] .................... A61K 31/445; C07D 211/94

[52] U.S. Cl. .................................... 514/320; 514/302; 514/326; 546/115; 546/196; 546/199

[58] Field of Search ........................ 546/199, 196, 115; 514/302, 320, 326

[56] References Cited

U.S. PATENT DOCUMENTS 4,335,122 6/1982 McFadden .......................... 546/196

FOREIGN PATENT DOCUMENTS 300908 1/1989 France ................................ 546/196

OTHER PUBLICATIONS

Chemical Abstr., vol. 101, 191691n, Nov. 19, 1984.

*Primary Examiner*—Mary C. Lee
*Assistant Examiner*—Jacqueline Haley
*Attorney, Agent, or Firm*—Morgan & Finnegan

[57] ABSTRACT

New benzopyran derivatives of general formula (I) in which:

$R_1$ denotes a hydrogen or halogen atom or a hydroxy, alkyloxy, nitro, amino, alkylsulphonamido, bis(alkylsulphonyl)amino, or acylamino radical, R denotes a radical of general formula:

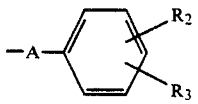

in which A denotes a single bond or a methylene radical and $R_2$ and $R_3$ which may be identical or different, denote a hydrogen or halogen atom or a hydroxy, alkyl, alkyloxy, nitro, amino, alkylsulphonamido, bis(alkylsulphonyl)amino, acylamino, sulphamoyl or cyano radical, or form together, when they are adjacent, a methylenedioxy or ethylenedioxy radical, or alternatively R denotes a 2-oxo-2H-benzimidazolyl radical, and R' and R'' are identical and denote hydrogen atoms or alkyl radicals, their isomeric forms and their preparation.

These new products are useful as antiarrhythmic and antifibrillating agents.

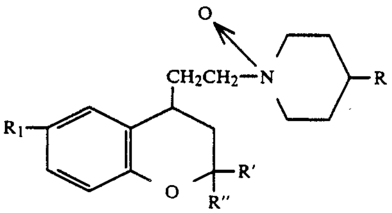

(I)

3 Claims, No Drawings

BENZOPYRAN DERIVATIVES AND PHARMACEUTICAL COMPOSITIONS CONTAINING THEM

DETAILED DESCRIPTION OF THE INVENTION

The present invention relates to new benzopyran derivatives of general formula:

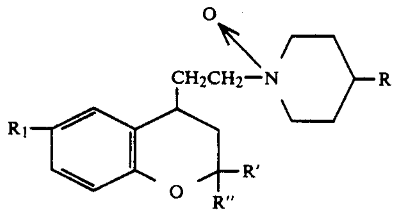

(I)

their preparation and to pharmaceutical compositions containing them.

In German Patent 3,300,004, a description has been given of 4-(aminomethyl)benzopyran derivatives which are active as hypotensives and muscle relaxants, and corresponding to the formula:

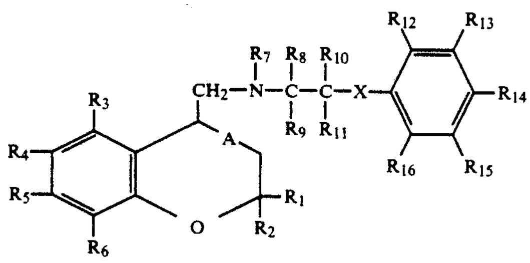

in which

A denotes, in particular, a single bond, $R_1$, $R_2$, $R_8$, $R_9$, $R_{10}$ and $R_{11}$ can denote hydrogen atoms, $R_3$, $R_4$, $R_5$ and $R_6$ can be hydrogen atoms or alkyloxy radicals, $R_{12}$ to $R_{16}$ can be, inter alia, hydrogen atoms or alkyloxy radicals, or 2 of these adjacent radicals can form a methylenedioxy radical, and $—NR_7—CR_8R_9—CR_{10}R_{11}—X—$ can denote a piperazinyl radical.

It has been found that the products of general formula (I) in which $R_1$ denotes a hydrogen or halogen atom or a hydroxy, alkyloxy, nitro, amino, alkylsulphonamido, bis(alkylsulphonyl)amino, or acylamino radical, R denotes a radical of general formula:

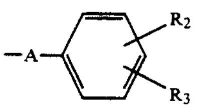

(II)

in which A denotes a single bond or a methylene radical and $R_2$ and $R_3$ which may be identical or different, denote a hydrogen or halogen atom or a hydroxy, alkyl, alkyloxy, nitro, amino, alkylsulphonamido, bis(alkylsulphonyl)amino, acylamino, sulphamoyl or cyano radical, or form together, when they are adjacent, a methylenedioxy or ethylenedioxy radical, or alternatively R denotes a 2-oxo-2H-benzimidazolyl radical, and R' and R'', which are identical, denote hydrogen atoms or alkyl radicals, as well as their salts, bring about an especially advantageous increase in the refractory periods, which corresponds to the antifibrillating effects of class III anti-arrhythmic products according to VAUGHAN WILLIAMS's classification.

In the general formula (I), when $R_1$, and $R_2$ and $R_3$ (in the symbol R), denote a halogen atom, the latter may be selected from fluorine, chlorine, bromine or iodine; when $R_1$, $R_2$ or $R_3$ denote or contain alkyl or acyl radicals, the latter may be linear or branched and they contain 1 to 4 carbon atoms.

It is understood that the products of general formula (I) possess isomeric forms, and that these isomers and the mixtures thereof fall within the scope of the present invention According to the invention, the products of general formula (I) may be prepared by oxidation of the benzopyran derivative of general formula:

(III)

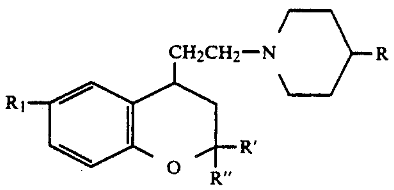

in which R, $R_1$, R' and R'' are defined as above, by any known method which does not adversely affect the remainder of the molecule.

The reaction is accomplished by means of an oxidizing agent such as an organic peracid, e.g. peracetic acid or monoperphthalic acid, in an organic solvent such as an ether (e.g. ethyl ether, tetrahydrofuran) or a chlorinated solvent (e.g. chloroform, dichloromethane) at a temperature of between 0° and 25° C. The oxidation may also be accomplished by means of hydrogen peroxide, working in an aqueous medium or in acetic acid or acetic anhydride at a temperature of between −50° and 25° C.

It is understood that, in the case where the molecule bears amino substituents, these substituents are protected prior to the reaction. The protection and removal of the protective radicals are performed according to the methods mentioned below.

The products of general formula (III) may be obtained by the action of a product of general formula:

(IV)

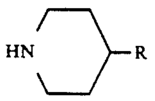

or its salt, in which R is defined as above, on a benzopyran derivative of general formula:

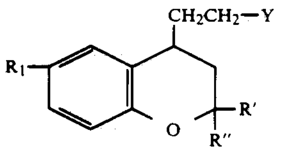

(V)

in which $R_1$, R' and R" are defined as above and Y denotes a halogen atom or an alkylsulphonyloxy or arylsulphonyloxy radical.

It is advantageous to work in the presence of an acid-acceptor agent. It is also possible to work without an acid-acceptor, in the presence of 2 equivalents of the product of general formula (IV).

When Y denotes a halogen atom, it may be selected from chlorine and bromine atoms.

When Y denotes an alkylsulphonyloxy radical, it denotes, in particular, a methylsulphonyloxy radical, and when it denotes an arylsulphonyloxy radical, it can be, inter alia, a p-toluenesulphonyloxy radical.

By way of an acid-acceptor, an alkali metal hydroxide or alkaline earth metal hydroxide (e.g. sodium hydroxide or potassium hydroxide), an alkali metal carbonate (e.g. sodium bicarbonate, potassium bicarbonate) or a nitrogenous organic base such as, e.g. triethylamine, is advantageously used.

The reaction is performed in an inert solvent such as a ketone (e.g. acetone, butanone), an ether (e.g. tetrahydrofuran or dioxane), an alcohol (e.g. methanol or ethanol), a hydrocarbon (e.g. hexane or toluene), acetonitrile, dimethylformamide or dimethylsulphoxide, or in a mixture of such solvents, at a temperature between 20° C. and the refluxing temperature of the reaction mixture.

It is understood that, in the cases where $R_1$, $R_2$ and/or $R_3$ (in R) denote an amino radical, the latter is protected beforehand. Similarly, when $R_2$ and/or $R_3$ denote a hydroxy radical, it is preferable to protect this radical prior to the reaction.

The protection is accomplished with any compatible group whose use and removal do not adversely affect the remainder of the molecule. It is performed, in particular, according to the methods described by T.W. Greene, Protective Groups in Organic Synthesis, A. Wiley - Interscience Publication (1981), or by Mc Omie, Protective Groups in Organic Chemistry, Plenum Press (1973).

The products of general formula (III) for which the radicals $R_1$, $R_2$ and/or $R_3$ denote a hydroxy radical may also be obtained from the corresponding product of general formula (I) for which the radical $R_1$, $R_2$ and/or $R_3$ to be converted denote an alkyloxy radical, by treatment in a concentrated acid medium.

The reaction is generally performed by treatment with hydrobromic acid, or a mixture of acids, e.g. by treatment with a hydrobromic acid/acetic acid mixture, at the refluxing temperature of the reaction mixture.

The products of general formula (III) for which the symbols $R_1$, $R_2$ and $R_3$denote an amino, alkylsulphonamido, bis(alkylsulphonyl)amino or acylamino radical may also be obtained by catalytic hydrogenation in an acid medium of the benzopyran derivative of general formula (I) for which the radical $R_1$, $R_2$ and/or $R_3$ to be converted denotes a nitro radical, and then, when it is desired to obtain a product of general formula (I), for which $R_1$, $R_2$ and/or $R_3$ denote an alkylsulphonamido, bis(alkylsulphonyl)amino or acylamino radical, the amino derivative obtained is converted by sulphonylation or by acylation, respectively.

The hydrogenation is advantageously performed at a temperature between 20° and 50° C., in an acid such as, e.g. acetic acid or hydrochloric acid, in an organic solvent such as an alcohol (e.g. methanol, ethanol, isopropanol), in a mixture of solvents or in an aqueous-organic medium (e.g. alcohol/water). It is also possible to work directly in the acid without the further addition of a solvent By way of a catalyst, palladium, platinum oxide or Raney nickel is generally used.

The reaction is optionally performed under pressure.

The sulphonylation or acylation is accomplished, respectively, by the action of an activated form of an acid $alkSO_3H$ or alk'COOH (alk and alk' being alkyl radicals), in particular the acid halide (e.g. acid chloride) or anhydride, and the reaction is carried out in the presence of an acid-acceptor, e.g. a nitrogenous organic base such as a trialkylamine (e.g. triethylamine) or such as pyridine, in an inert organic solvent such as a chlorinated solvent (e.g. dichloromethane, chloroform), an ether (e.g. ethyl ether, tetrahydrofuran) or in a mixture of these solvents, at a temperature of between −70 and +40° C.

The reaction is optionally performed under nitrogen.

When it is desired to obtain the product of general formula (III) for which $R_1$, $R_2$ and/or $R_3$ denote a bis-(alkylsulphonyl)amino radical, the reaction is performed in the presence of 2 equivalents of the corresponding sulphonic acid derivative.

The products of general formula (IV) may be prepared according to the methods described by:

V. NACCI et al , Farmaco Ed. Sci., 328(5), 399 (1973),

P.C. JAIN et al., J. Med. Chem., 10, 813 (1967),

J. CRAIG et al., Org. Synth., 5, 88 (1973),

Dutch Patent Application 65 10 107

U.S. Pat. No. 4,421,753 described below in the examples, or by working analogously to these methods.

The products of general formula (V) may be obtained by the action of a halogenating agent or of an activated form of an alkylsulphonic or arylsulphonic acid on a 4-(hydroxyalkyl)benzopyran of general formula:

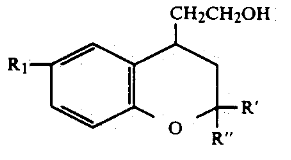

(VI)

in which $R_1$, R', and R" are defined as above.

When it is desired to prepare a product of general formula (V) for which Y is a halogen atom, the halogenating agents may be selected from thionyl chloride and halogenated derivatives of phosphorus, such as phosphorus oxychloride or phosphorus tribromide. It is also possible to react allyl bromide in the presence of N,N'-carbonyldiimidazole.

When it is desired to prepare a product of general formula (V) in which Y is alkylsulphonyloxy or arylsulphonyloxy, the anhydride or halide of the corresponding acid is advantageously reacted.

The reaction is generally performed in the presence of a nitrogenous organic base such as triethylamine or pyridine, in an organic solvent such as a chlorinated solvent (e.g. methylene chloride) or an ether (e.g. tetrahydrofuran, dioxane), working at a temperature between 0° C. and the refluxing temperature of the reaction mixture.

The products of general formula (V) in which $R_1$ is a nitro radical may be obtained by nitration of a derivative of general formula (V) for which $R_1$ is a hydrogen atom.

The reaction is advantageously performed using a nitric acid/acetic acid mixture at a temperature of between 0° and 20° C.

The 4-(hydroxyalkyl)benzopyran derivative of general formula (VI) may be prepared by reduction of the corresponding ester of general formula:

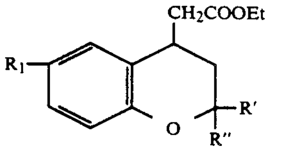
(VII)

in which $R_1$, R' and R" are defined as above.

The reaction is generally performed using lithium aluminium hydride in an organic solvent such as an ether (e.g. tetrahydrofuran) at a temperature of between 0° and 30° C.

The ester of general formula (VII) may be obtained by reduction of the benzopyran derivative of general formula:

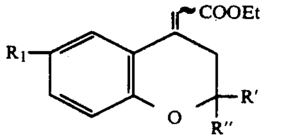
(VIII)

in which $R_1$, R' and R" are defined as above. The reaction is performed by catalytic hydrogenation in the presence of palladium, in an organic solvent such as an alcohol (e.g. methanol, ethanol), at a temperature between 10° and 50° C. The benzopyran derivative of general formula (VIII) may be prepared by WITTIG reaction, starting with a 4-chromanone derivative of general formula:

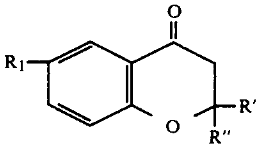
(IX)

in which $R_1$, R' and R" are defined as above.

The reaction is advantageously performed using ethyl diethylphosphonoacetate in the presence of sodium hydride, in an organic solvent such as an ether (e.g. tetrahydrofuran or dimethoxyethane) at a temperature between 0° C. and the refluxing temperature of the reaction mixture.

The 4-chromanone derivative of general formula (IX) in which R is other than hydrogen may be prepared by application of the method described by PFEIFFER et al., Chem. Ber., 58 (1954), or according to the methods described by G.P. Ellis, Heterocyclic compounds, chromenes, chromanones and chromones, John Wiley and Sons (1977).

The 4-chromanone derivative of general formula (IX) in which R is a fluorine atom may be prepared according to the method described in French patent application No. 2,588,860.

The 4-chromanone derivatives of general formula (IX) in which $R_1$ is an amino, alkylsulphonamido, bis(alkylsulphonyl)amino or acylamino radical may be obtained from the 4-chromanone derivative of general formula (IX) for which $R_1$ is a nitro radical, by working analogously to the methods described for the preparation of the products of the general formula (III) for which the radical $R_1$ is defined as above.

2,2-Dimethyl-4-chromanone may be obtained according to the method described in Belgian Patent No. 844,943.

The enantiomers of the products according to the invention may be separated according to known methods.

The procedure is performed, in particular, by preparation of the enantiomer of the hydroxyethylbenzopyran derivative of general formula (VI), which is converted to a product of general formula (I) according to the process described above.

The optically active derivative of general formula (VI) is obtained by preparation of an optically active amide of general formula:

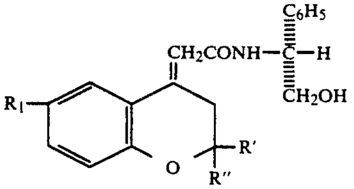
(X)

in which $R_1$, R' and R" are defined as above, separation of the isomers by chromatography, hydrolysis of the desired isomer and then reduction of the acid obtained.

The hydrolysis of the isomer of the product of general formula (X) may be accomplished by any known method which does not adversely affect the remainder of the molecule; it is advantageous to work in an acid medium (mixtures of acetic acid and hydrochloric acid) at the refluxing temperature of the reaction mixture.

The reduction of the acid to the alcohol is carried out according to the usual methods. In particular, diborane is used by way of a reducing agent and it is advantageous to work in an ether such as tetrahydrofuran at temperatures of between 0° and 30° C.

The product of general formula (X) may be prepared from the acid of general formula:

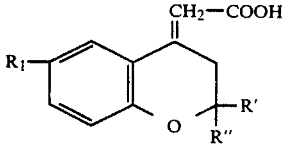
(XI)

in which $R_1$, R' and R" are defined as above, by any known method for preparing an amide from an acid.

The reaction is advantageously performed using the acid chloride of general formula (XI) (which may be prepared in situ) in an inert organic solvent such as a chlorinated solvent (e.g. dichloromethane) in the presence of an acid-acceptor agent such as a nitrogenous organic base (e.g. triethylamine), at a temperature of between 0° and 30° C.

The acid of general formula (XI) may be obtained from the corresponding ester by any known method for obtaining an acid from an ester without affecting the remainder of the molecule.

Saponification of the ester of general formula (VII) is performed, in particular, with potassium hydroxide, in methanol at the refluxing temperature of the reaction mixture.

The acid chloride is prepared by treating the corresponding acid with thionyl chloride at the refluxing temperature of the reaction mixture.

The new benzopyran derivatives according to the invention may be purified, where appropriate, by physical methods such as crystallization or chromatography.

The products according to the invention exhibit especially advantageous anti-arrhythmic and antifibrillating properties characteristic of VAUGHAN WILLIAMS's class III, resulting in prolongation of the refractory periods.

They produce, in particular, in vitro on guinea pig papillary muscle, an increase of between 5% and values above 50% in the duration of the initial action potential, according to the measuring technique for recording intracellular action potential described by E. CORABOEUF and S. WEIDMANN, C.R. Soc. Biol., 143, 1329 (1949).

Moreover, benzopyran derivatives according to the invention exhibit low toxicity. They have been generally shown to be non-toxic at 300 mg/kg when administered orally to mice.

EXAMPLES

The following example illustrates the present invention:

EXAMPLE

A solution of m-chloroperbenzoic acid (2.6 g) in dichloromethane (40 cc) is added dropwise to a solution, cooled to between 0° and 5° C., of 1-[2-(3,4- dihydro-2H-1-benzopyran -4-yl) ethyl]-4-(3,4-dimethoxyphenyl)piperidine in dichloromethane (30 cc). (Solution prepared from the hydrochloride (5 g) by neutralization with 1N sodium hydroxide solution (15 cc)).

After 1 hour 30 minutes at room temperature, m-chloroperbenzoic acid (1 g) is added again and the mixture is left for a further hour at room temperature.

The reaction mixture is then washed with potassium carbonate solution (5 M) (100 cc) and thereafter with water (50 cc). The methylene chloride phase is separated and then dried over magnesium sulphate.

After filtration and concentration under reduced pressure (5.2 kPa), an oil is obtained which is then chromatographed on a column 2.5 cm in diameter containing silica gel (32–63 μ) (50 g), using as eluent a dichloromethane/isopropanol mixture (80:20 by volume) up to the first 45 fractions (fraction size 30 cc) and a dichloromethane/isopropanol mixture (60:40 by volume) for the last 15 fractions.

The fractions between 300 cc and 1.8 liters are collected and concentrated to dryness The oil obtained is solubilized in the heated state in isopropyl acetate. The solution is filtered and then treated with ethyl ether until persistent cloudiness is produced After scratching, 1-[2-(3,4-dihydro-2H-1-benzopyran-4-yl)ethyl]-4-(3,4-dimethoxyphenyl)-piperidine N-oxide (3.22 g) is obtained in the form of a white solid, m.p. 97° C.

1-[2-(3,4-Dihydro-2H-1-benzoypyran-4-yl)ethyl]-4-(3,4-dimethoxyphenyl)piperidine hydrochloride may be prepared in the following manner:

4-(2-Bromoethyl)-3,4-dihydro-2H-benzopyran (1.5 g), 4-(3,4-dimethoxyphenyl)piperidine dihydrochloride (1.5 g), dry potassium carbonate (1.61 g) and potassium iodide (1 g) in 2-butanone (50 cc) are heated to reflux for 3 hours.

The reaction mixture is filtered on sintered glass and the solvent is then evaporated off under reduced pressure (5.2 kPa). The oil obtained is extracted with dichloromethane (80 cc) and the organic phase is then washed with IN sodium hydroxide solution (10 cc), washed with water and then dried over magnesium sulphate.

After evaporation, the oil obtained is taken up with ethanol (15 cc) and a 2N solution (2.7 cc) of hydrochloric acid in ethanol is added.

1-[2-(3,4-Dihydro-2H-1-benzopyran-4-yl)ethyl]-4-(3,4-dimethoxyphenyl)piperidine hydrochloride (1.6 g) is thereby obtained in the form of a white solid (m.p. 237 C.).

4-(3,4-Dimethoxyp-henyl)piperidine may be prepared according to the method described by V. NACCI et al., Farmaco Ed. Sci., 328(5), 399–410 (1973).

2-Bromo-4-ethyl-3,4-dihydro-2H-benzopyran may be prepared in the following manner:

2-(3,4-Dihydro-2H-1-benzopyran-4-yl)ethanol (13.8 g), then allyl bromide (91.2 g) and finally N,N'-carbonyldiimidazole (12.6 g) are added with stirring to acetonitrile (115 cc).

The mixture is stirred for 3 hours 10 minutes at approximately 20° C. and then 2 hours under reflux The reaction mixture is then concentrated under reduced pressure (5.2 kPa) and the residue obtained is chromatographed on a column 5.5 cm in diameter containing silica gel (200 g), eluting with dichloromethane (550 cc) and collecting 100 cc fractions. The fractions between 350 and 550 cc are concentrated to dryness.

4-(2-Bromoethyl)-3,4-dihydro-2H-benzopyran (17.7 g) is thereby obtained in the form of a light brown oil.

Proton NMR spectrum (250 MHz, $CDCl_3$, δ in ppm):

6.8 to 7.2 (mt, 4H aromatic)

4.21 (mt, $—O—\underline{CH_2}—$)

3.55 (mt, $—\underline{CH_2}—Br$)

3.08 (mt, $—\underline{CH}—$)

1.92 and 2.92 (mt, $—CH_2—$at the 3-position)

2.08 and 2.34 (mt, $—\underline{CH_2}CH_2Br$)

2-(3,4-Dihydro-2H-1-benzopyran-4-yl)ethanol may be prepared in the following manner:

Tetrahydrofuran (500 cc) is added to lithium aluminium hydride (5.96 g) and the mixture is cooled to 0° C. Ethyl 2-(3,4-dihydro-2H-1-benzopyran-4-yl)ethanoate ( 17.25 g) in tetrahydrofuran (60 cc) is then added with stirring.

After 1 hour's stirring at 20° C., the mixture is hydrolyzed with stirring by adding hydrated sodium sulphate ($10\ H_2O$) until precipitation occurs, and the reaction mixture is then left to stand for 15 hours.

After filtration of the precipitate formed and evaporation of the solvent under reduced pressure, 2-(3,4-dihydro-2H-1-benzopyran-4-yl)ethanol (13.8 g) is isolated in the form of a brown oil.

NMR spectrum (250 MHz, $CDCl_3$, δ in ppm):

6.8 to 7.2 (mt, 4H aromatic)

4.22 (mt, $—O—\underline{CH_2}—$)

3.83 (mt, $—\underline{CH_2}—OH$)

3.04 (mt, —CH—)

1.83 and 2.90 (mt, $—CH_2—$ at the 3-position and $—CH_2—CH_2OH$)

1.62 (s, —OH)

Ethyl (3,4-dihydro-2H-1-benzopyran-4-yl)ethanoate may be prepared in the following manner:

Ethyl (E,Z)-(3,4-dihydro-2H-1-benzopyran-4-ylidene)acetate (50.6 g) in methanol (1 liter) is hydrogenated at 20° C. under atmospheric pressure in the presence of palladium (5.06g) on charcoal (10%).

After filtration on Kieselguhr and concentration to dryness under reduced pressure (5.2 kPa), ethyl (3,4-dihydro-2H-1-benzopyran-4-yl)ethanoate (48.8 g) is obtained in the form of a pale yellow oil.

NMR spectrum (250 MHz, $CDCl_3$, δ in ppm):

6.75 to 7.2 (mt 4H aromatic)

4.98 (q+mt, $—O—CH_2—+—CO—OCH_2—CH_3$)

3.37 (mt, —CH—)

2.53 and 2.82 (dd, $—CH_2—CO—$)

1.87 and 2.18 (mt, $—CH_2—$ at the 3-position)

1.30 (t, $—COO—CH_2—CH_3$)

Ethyl (E,Z)-(3,4-dihydro-2H-1-benzopyran-4-ylidene)acetate may be prepared in the following manner:

With stirring, sodium hydride (80%) (20.4 g) is added to anhydrous tetrahydrofuran (1 liter) and ethyl diethylphosphonoacetate (153 g) is then added in small portions while the temperature of the reaction mixture is maintained at around 20° C. The light yellow solution thereby obtained is then treated with 4-chromanone (45 g) in anhydrous tetrahydrofuran (100 cc) while the temperature is maintained below 0° C. After 22 hours at 20° C., the reaction mixture is concentrated under reduced pressure and the oil obtained is then extracted with dichloromethane (2×700 cc). The organic phase is washed with water, then dried over magnesium sulphate and concentrated to dryness under reduced pressure. The evaporation residue is chromatographed on a column 9 cm in diameter containing silica gel (1.6 kg), eluting with a cyclohexane/ethyl acetate mixture (90:10 by volume) (6.3 liters) and collecting 250 cc fractions. The fractions between 2.8 and 6.3 liters are concentrated to dryness.

A mixture (50.6 g) of E and Z isomers of ethyl (3,4-dihydro-2H-1-benzopyran-4-ylidene)acetate is thereby obtained in the form of a pale yellow oil.

NMR spectrum (400 MHz, $CDCl_3$, δ in ppm): E isomer (75%):

6.8 to 7.61 (mt, 4H aromatic)

6.36 (s, =CH—CO—)

4.23 (mt, $—O—CH_2—$)

4.23 (mt, $—CO—OCH_2—CH_3$)

3.41 (mt, $—CH_2—$ at the 3-position)

1.32 (mt, $—CO—OCH_2—CH_3$)

Z isomer (25%):

6.8 to 7.83 (mt, 4H aromatic)

5.61 (s, =CH—CO—)

4.38 (t, $—O—CH_2—$)

4.23 (mt, $—CO—OCH_2—CH_3$)

2.65 (t, $—CH_2—$ at the 3-position)

1.32 (mt, $—CO—OCH_2—CH_3$)

The present invention also relates to pharmaceutical compositions consisting of a product of general formula (I), in the pure state or in the form of a combination with any other pharmaceutically compatible product, which can be inert or physiologically active. The compositions according to the invention may be used orally or parenterally.

As solid compositions for oral administration, tablets, pills, powders or granules may be used. In these compositions, the active product according to the invention (optionally combined with another pharmaceutically compatible product) is mixed with one or more inert adjuvants or diluents such as sucrose, lactose or starch. These compositions can also comprise substances other than diluents, e.g. a lubricant such as magnesium stearate.

As liquid compositions for oral administration, emulsions of a pharmaceutically acceptable nature, solutions, suspensions, syrups and elixirs containing inert diluents such as water or liquid paraffin may be used. These compositions can also comprise substances other than diluents, e.g. wetting products, sweeteners or flavorings.

The sterile compositions for parenteral administration can preferably be solutions, aqueous or non-aqueous, suspensions or emulsions. As a solvent or vehicle, water, propylene glycol, a polyethylene glycol, vegetable oils, especially olive oil, injectable organic esters, e.g. ethyl oleate, or other suitable organic solvents may be employed. These compositions can also contain adjuvants, especially wetting agents, tonicity regulators, emulsifiers, dispersants and stabilizers. The sterilization may be carried out in several ways, e.g. by aseptic filtration, by incorporating sterilizing agents in the composition, by irradiation or by heating. They may also be prepared in the form of sterile solid compositions which can be dissolved at the time of use in a sterile injectable medium.

The pharmaceutical compositions according to the invention are especially useful in human therapy. They enable heart rhythm disorders due to re-entry phenomena, treated or untreated, to be reduced in treatments following myocardial infarction, as well as in chronic anginal states and ischaemic type cardiopathies.

Generally speaking, the doctor will determine the dosage he considers most appropriate in accordance with the age, weight and other factors characteristic of the subject to be treated.

In general, the doses are between 0.25 and 1.5 g per day of active product administered orally or intravenously for an adult.

The example which follows, given without implied limitation, illustrates a composition according to the invention.

EXAMPLE

Tablets having the following composition are prepared:

| | |
|---|---|
| 1-[2-(3,4-dihydro-2H-1-benzopyran-4-yl)ethyl]-4-(3,4-dimethoxyphenyl)piperidine N-oxide | 130 mg |
| lactose | 50 mg |
| excipient | q.s. 250 mg |

Although the invention has been described in conjunction with specific embodiments, it is evident that many alternatives and variations will be apparent to those skilled in the art in light of the foregoing description. Accordingly, the invention light of the foregoing description. Accordingly, the invention is intended to embrace all of the alternatives and variations that fall within the spirit and scope of the appended claims. The above references are hereby incorporated by reference.

We claim:

1. A benzopyran derivative, which is of the formula:

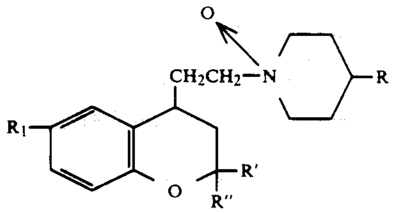

in which $R_1$ denotes a hydrogen or halogen atom or a hydroxy, alkyloxy, nitro, amino, alkylsulphonamido, bis(alkylsulphonyl)amino, or alkylcarbonylamino radical, R denotes a radical of general formula:

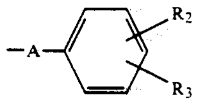

in which A denotes a single bond or a methylene radical and $R_2$ and $R_3$ which may be identical or different, denote a hydrogen or halogen atom or a hydroxy, alkyl, alkyloxy, nitro, amino, alkylsulphonamido, bis(alkylsulphonyl)amino, alkylcarbonylamino, sulphamoyl or cyano radical, or form together, when they are adjacent, a methylenedioxy or ethylenedioxy radical, or alternatively R denotes a 2-oxo-2H-benzimidazolyl radical, and R' and R'' are identical and denote hydrogen atoms or alkyl radicals, on the understanding that the alkyl and alkylcarbonyl, radicals mentioned above contain 1 to 4 carbon atoms in a straight or branched chain, its isomeric forms or the mixtures thereof.

2. 1-[2-(3,4-Dihydro-2H-1-benzopyran-4-yl)ethyl]-4-(3,4-dimethoxyphenyl)piperidine N-oxide, its isomeric forms or the mixtures thereof.

3. A pharmaceutical composition, which comprises an anti-arrhythmic or antifibrillating effective amount of a benzopyran derivative according to claim 1, in combination with a pharmaceutically acceptable adjuvant or diluent.

* * * * *